| United States Patent [19] | [11] | 4,139,710 |
|---|---|---|
| Drewes | [45] | Feb. 13, 1979 |

[54] PREPARATION OF HEXAHYDROINDAZOLONES

[75] Inventor: Harold R. Drewes, Newark, Del.

[73] Assignee: E. I. Du Pont de Nemours and Company, Wilmington, Del.

[21] Appl. No.: 776,719

[22] Filed: Mar. 11, 1977

[51] Int. Cl.$^2$ .......................................... C07D 231/56
[52] U.S. Cl. ................................. 548/359; 260/557 R
[58] Field of Search ........................................ 548/359

[56] References Cited

U.S. PATENT DOCUMENTS 2,104,348  6/1933  Lee et al. ............................. 548/359

FOREIGN PATENT DOCUMENTS 961037  6/1964  United Kingdom ..................... 548/359
987597  3/1965  United Kingdom ..................... 548/359

*Primary Examiner*—Natalie Trousof
*Assistant Examiner*—Jane T. Fan

[57] ABSTRACT

This invention relates to a novel process for the preparation of hexahydroindazolones useful as herbicides by condensation of an aromatic hydrazine source with a cyclohexanone 2-carboxamide, under controlled reaction conditions.

9 Claims, No Drawings

PREPARATION OF HEXAHYDROINDAZOLONES

BACKGROUND OF THE INVENTION

This invention relates to a novel process for preparation of hexahydroindazolones. The production of such hexahydroindazolones has been known in the past. Typical of the processes utilized was one involving an intermediate whose preparation was taught by H. R. Snyder et al., Org. Syn. Coll. Vol. II, 531–534 (1943) wherein ethyl cyclohexanone-2-carboxylate was prepared in an organic solvent from cyclohexanone and diethyl oxalate.

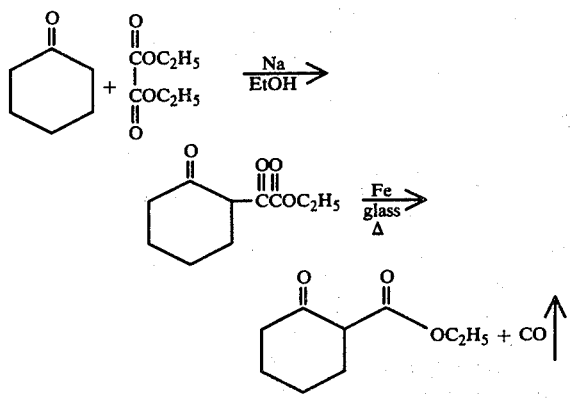

The ethyl cyclohexanone-2-carboxylate and aromatic hydrazines could then be reacted to form hexahydroindazolones.

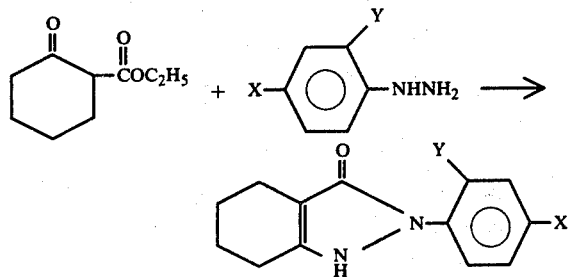

There are problems associated with such a reaction in that the keto ester is difficult to prepare and is not readily available in large quantities. Additionally, there are problems associated with the use of organic solvents. The Fe and glass catalyzed decarbonylation can be difficult to control and dangerous pressure increases may occur. For reasonable yields, the intermediate glyoxylic ester must be distilled and can decarbonylate during distillation if traces of metal are present. The use of organic solvent presents problems of increased use and disposal costs relative to water. It also requires the use of the free hydrazine base for solubility reasons; any time the free base is liberated there is the risk of decomposition through oxidation.

Since the 2-aryl-1,2,4,5,6,7-hexahydro-3H-indazol-3-ones are important intermediates for making herbicides, an efficient process for preparing the indazolones in high yield is needed.

SUMMARY OF THE INVENTION

According to the instant invention, such a process for preparing 2-aryl-1,2,4,5,6,7-hexahydro-3H-indazol-3-ones has been discovered. Unexpectedly, the indazolones may be prepared by condensation (reaction) of an aromatic hydrazine source such as a free hydrazine base, a hydrazine acid addition salt or anionic hydrazine salt with cyclohexanone 2-carboxamide. In my copending application BA-8215, an improved method for producing cyclohexanone 2-carboxamide is disclosed. Water and ammonia are liberated during the formation of the indazolones; typically, the indazolones are produced in yields in excess of 85% by the instant reaction.

More specifically, the process for preparation of the indazolones is characterized by the following steps: an aromatic hydrazine source is added to a protic or aprotic solvent followed by cyclohexanone 2-carboxamide. A stoichiometric excess of either the aromatic hydrazine source or cyclohexanone 2-carboxamide may be used. For economic reasons, one equivalent of hydrazine per equivalent of carboxamide is preferred. The pH, temperature and pressure of the reaction are adjusted such that the reaction proceeds at a convenient rate without causing decomposition of either the starting material or product. Elevated temperatures are utilized. Protic solvents are preferred for the reaction; water is the most preferred solvent. Reaction temperatures from ambient to the boiling point of the solvent are operable. Typically, ambient pressures are utilized but if desired elevated or reduced pressure may be utilized. The reaction may take place in any convenient vessel. Reaction time may vary between about 0.5 to 4.0 hours. It is understood, however, that other factors such as quantity of reactants, etc., may cause wide variation in reaction time.

DETAILED DESCRIPTION OF THE INVENTION

Several different aromatic hydrazine sources may be utilized for the reaction of the instant invention. They include free hydrazine bases such as

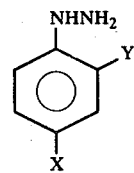

wherein:
Y = hydrogen, fluorine, or chlorine
X = fluorine, chlorine, bromine, iodine, cyano, methoxy or nitro,
hydrazine acid addition salts such as

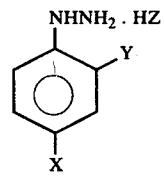

II wherein:
X and Y are as above
Z = chloride or sulfate
or an anionic hydrazine salt such as

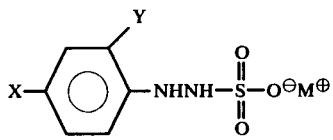

wherein:
X and Y are as above;
M = sodium, potassium, calcium, lithium or magnesium.

For convenience, it is preferred to use a free hydrazine base or hydrazine acid addition salt. Most preferred are hydrazine acid addition salts:

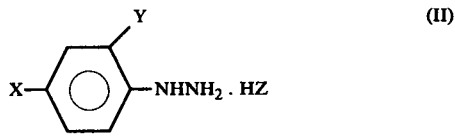

More preferred values for Y are hydrogen or fluorine and for X are fluorine, chlorine, bromine or methoxy.

In a most preferred embodiment of the instant invention Y is fluorine and X is chlorine; in another most preferred embodiment Y is hydrogen and X is chlorine; in still another most preferred embodiment, Y is fluorine and X is bromine.

The reaction, when utilizing a free hydrazine base would proceed as follows:

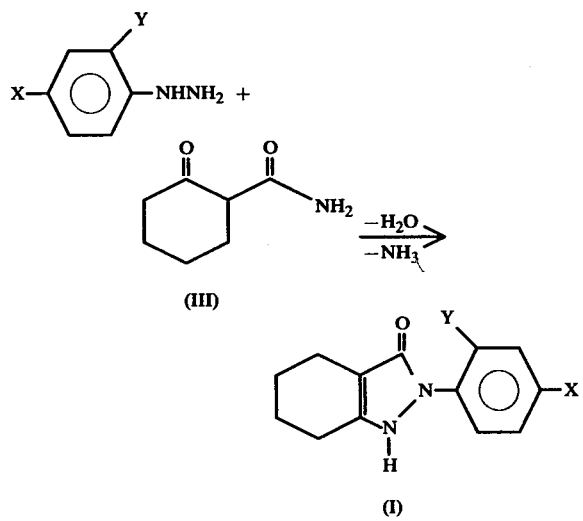

where
Y is hydrogen, fluorine or chlorine; and
X is fluorine, chlorine, bromine, iodine, cyano, methoxy or nitro.

The cyclohexanone 2-carboxamide (III) may be prepared according to the process described in the East German Pat. No. 112,987. Preferably, it may be prepared by the process described in copending application BA-8215.

The protic solvents are preferred for the instant reaction for the following reasons. The hydrazine acid addition salts are more soluble in protic solvents — especially H$_2$O. To use organic solvents, the salts must be neutralized and extracted from the aqueous solution in which they were prepared; any time the free hydrazine is liberated, it is subject to oxidation and decomposition. Additionally, the cyclohexanone-2-carboxamide is virtually insoluble in most non-protic solvents.

Typical protic solvents which may be utilized include: H$_2$O, ethanol, methanol, ethylene glycol, propanol, isopropanol, butanol and other glycols or alcohols.

More preferred solvents are water and ethanol.

Of the protic solvents the most preferred for reasons of economy and availability is water. The use of β-keto amide III, which is water soluble makes the use of water as a solvent possible where ordinarily it would not be.

The preferred reaction temperature for economic reasons and convenience would be between about 80° and 100° C. Needless to say, the reaction is operable outside of this range. Ambient pressures are most preferred for economy and convenience.

The reaction vessel may be glass, glass lined, or of a material not attacked or corroded by mineral acids.

The product is recovered by filtration, washing and drying. Washing may be accomplished with water, followed by a non-polar solvent such as toluene, xylene or hexane.

In a preferred embodiment of the instant invention, an aqueous slurry of one equivalent of an aromatic hydrazine acid addition salt, such as that of formula II, wherein Y is F, and X is Cl is stirred and heated at 90°-100° C. An aqueous solution of one equivalent of cyclohexanone 2-carboxamide at 90°-100° C. is added over about 5 minutes. The reactants are then stirred at a temperature of about 80°-100° C. for a period of about 1½ to 2 hours. The resulting precipitate is filtered while hot, washed with toluene and dried to give

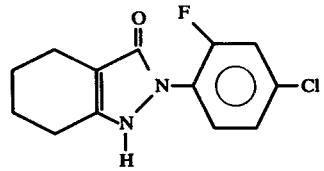

in 85 to 95% yield.

In the following examples all parts are by weight and temperature in ° C. unless otherwise specified.

EXAMPLE

Preparation of 2-(4-chloro-2-fluorophenyl)-1,2,4,5,6,7-hexahydro-3H-indazol-3-one (a) Preparation of 4-chloro-2-fluorophenyl hydrazine hydrochloride (1) Preparation of the diazonium salt To 2000 parts of concentrated hydrochloric acid and 3500 parts of water was added 1020 parts of 4-chloro-2-fluoro-aniline. The reactants were heated to 50° for 1 hr. with stirring. The resulting slurry was cooled to 0°-5° with an ice-water bath. To this slurry was added 500 parts of sodium nitrite in 1000 parts water over 1.5 min. and stirred at 5°-10° for 0.5-1.0 hr. Excess sodium nitrite was decomposed with sulfamic acid.

(2) Preparation of 2-(4-chloro-2-fluorophenyl)hydrazine hydrochloride

In a second vessel were charged 3500 parts water, 1960 parts sodium bisulfite and a sufficient quantity of 10 N sodium hydroxide to adjust the pH to 6.7 ± 0.2. (approximately 700 parts). The temperature was adjusted to 50°. To this solution was charged the freshly prepared solution of the diazonium salt over a period of 30 min. The resulting solution was heated to 75° ± 2° for 1.5 hr. while maintaining the pH at 6.7 ± 0.2. Fourteen parts of sodium hydrosulfite was added and heating was continued for 30 min. To this solution containing sodium 2-(4-chloro-2-fluorophenyl)hydrazine sulfonate was added 2200 parts of concentrated HCl and heating continued at 75° ± 2° for 2 hours to give a suspension containing 2-(4-chloro-2-fluorophenyl)hydrazine hydrochloride.

(b) Preparation of cyclohexanone 2-carboxamide

60 Parts of urea were mixed with 18 parts of ammonium carbonate and were added in portions to 392 parts of cyclohexanone at 135°. The mixture was allowed to reflux with water continuously being separated with a Dean Stark trap. Water elimination was complete in 80 minutes; 36.5 parts of water were collected. Heating was discontinued and an aliquot was withdrawn. The product (370 parts) was poured into pans. It solidified quickly. Analysis using liquid chromatography showed 183.5 parts of spirolactam (yield = 83%). 367 Parts of the crude product were added to 1150 parts of water at 99°, and the pH of the mixture was adjusted to 1.0 using 44 parts of 50% sulfuric acid. Cyclohexanone was removed from the mixture by steam distillation while maintaining a pH of 0.9–1.0 by dropwise addition of 155 parts of acid. 76 Parts of cyclohexanone were collected in 20 minutes, after which the pH of the reaction mixture was adjusted to 5 using sodium hydroxide. Analysis of the aqueous product (1337 parts) showed a concentration of 7.8% of cyclohexanone carboxamide.

OVERALL YIELD DETERMINED BY LC ANALYSIS: 76%.

(c) Indazolone formation

The pH of the 4-chloro-2-fluorophenylhydrazine hydrochloride slurry was adjusted to 3.8–4.0 and the temperature was raised to 90°–95°. To this mixture was added an aqueous solution (preheated to 90°–95°) of 1118 parts of cyclohexanone-2-carboxamide prepared as previously described. The resulting mixture was heated for 1–2 hr at 90°–95° during which time the product precipitated from solution. The product was isolated by filtration, washed by digestion with toluene and air-dried to give 1771 parts of an indazolone, an off-white solid mp 179-182 which was 2-(4-chloro-2-fluorophenyl)-1,2,4,5,6,7-hexahydro-3H-indazol-3-one.

YIELD: DETERMINED BY GC ANALYSIS: 92.7%.

What is claimed is:

1. A process for the preparation of 2-aryl-1,2,4,5,6,7-hexahydro-3H-indazol-3-one which comprises contacting under reaction conditions in the presence of water, an aromatic hydrazine source with cyclohexanone 2-carboxamide and recovering the resulting 2-aryl-1,2,4,5,6,7-hexahydro-3H-indazol-3-one.

2. The process of claim 1 wherein the aromatic hydrazine source is selected from the group consisting of free hydrazine base, hydrazine acid addition salt or anionic hydrazine salt.

3. The process of claim 1 wherein the aromatic hydrazine source is a hydrazine acid addition salt.

4. The process of claim 3 wherein the hydrazine acid addition salt is selected from compounds of the formula

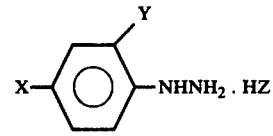

and the resulting 2-aryl-1,2,4,5,6,7-hexahydro-3H-indazol-3-one is selected from compounds having the formula

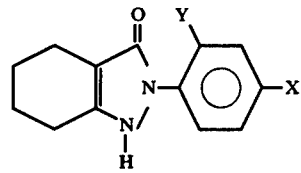

wherein Y is hydrogen, fluorine or chlorine, X is fluorine, chlorine, bromine, iodine, cyano, methoxy or nitro and Z is chloride or sulfate.

5. The process of claim 4 wherein Y is fluorine and X is bromine.

6. The process of claim 4 wherein Y is hydrogen and X is chlorine.

7. The process of claim 4 wherein Y is fluorine and X is chlorine.

8. The process of claim 4 wherein the reaction takes place at a temperature of about 80°–100° C.

9. A process for preparing 2-(4-chloro-2-fluorophenyl)-1,2,4,5,6,7-hexahydro-3H-indazol-3-one which comprises contacting a 4-chloro-2-fluorophenyl hydrazine acid addition salt at a temperature of about 80°–100° C. for a period of about 0.5 to 4 hours with cyclohexanone 2-carboxamide, said contact taking place in water, and recovering said indazolone.

* * * * *